(12) United States Patent
Cant et al.

(10) Patent No.: US 9,227,006 B2
(45) Date of Patent: Jan. 5, 2016

(54) NON-PENETRATING NOZZLE

(75) Inventors: Joseph Richard Cant, Naples, FL (US); Gary Michael Wilson, Naples, FL (US)

(73) Assignee: STERILAB, INC., Naples, FL (US)

( * ) Notice: Subject to any disclaimer, the term of this patent is extended or adjusted under 35 U.S.C. 154(b) by 458 days.

(21) Appl. No.: 13/700,652

(22) PCT Filed: May 27, 2011

(86) PCT No.: PCT/US2011/038375
§ 371 (c)(1),
(2), (4) Date: Nov. 28, 2012

(87) PCT Pub. No.: WO2011/150349
PCT Pub. Date: Dec. 1, 2011

(65) Prior Publication Data
US 2013/0090629 A1    Apr. 11, 2013

Related U.S. Application Data

(60) Provisional application No. 61/349,450, filed on May 28, 2010, provisional application No. 61/445,126, filed on Feb. 22, 2011.

(51) Int. Cl.
*A61M 31/00* (2006.01)
*A61M 3/02* (2006.01)

(52) U.S. Cl.
CPC ............ *A61M 3/0233* (2013.01); *A61M 3/0279* (2013.01); *A61M 3/0262* (2013.01); *A61M 31/00* (2013.01); *A61M 2210/1064* (2013.01)

(58) Field of Classification Search
CPC ...................... A61M 2210/1064; A61M 31/00; A61M 3/0233; A61M 3/0262; A61M 3/0279; A61M 3/02
USPC ............................................ 604/514, 911, 37
See application file for complete search history.

(56) References Cited

U.S. PATENT DOCUMENTS

| | | | |
|---|---|---|---|
| 655,540 | A | 8/1900 | Arlt |
| 1,940,122 | A | 12/1933 | Gardner |
| 1,969,831 | A | 8/1934 | Williams |
| 2,005,289 | A | 6/1935 | Ellsworth |
| 4,709,705 | A * | 12/1987 | Truglio .......................... 600/563 |

OTHER PUBLICATIONS

International Search Report, International Application No. PCT/US2011/038375, Sep. 29, 2011, two pages.

* cited by examiner

*Primary Examiner* — Kevin C Sirmons
*Assistant Examiner* — Deanna K Hall
(74) *Attorney, Agent, or Firm* — Howard & Howard Attorneys PLLC

(57) ABSTRACT

A device (10) administers a fluid (23) from a container (12) into a human cavity or animal cavity (66). The device includes a nozzle (20) configured to be placed in external contact with tissue surrounding an orifice (58) without penetrating the orifice. The nozzle includes a discharge opening (40), through which the fluid is ejected into the cavity, a base (24) disposed opposing the discharge opening, and a side wall (26) that extends from the discharge opening towards the base and configured so that the tissue surrounding the orifice conforms to the shape of the side wall to form a leaktight seal between the tissue and the orifice. An interior conduit (30) is disposed within the side wall and configured to deliver the fluid from the container to the discharge opening.

17 Claims, 18 Drawing Sheets

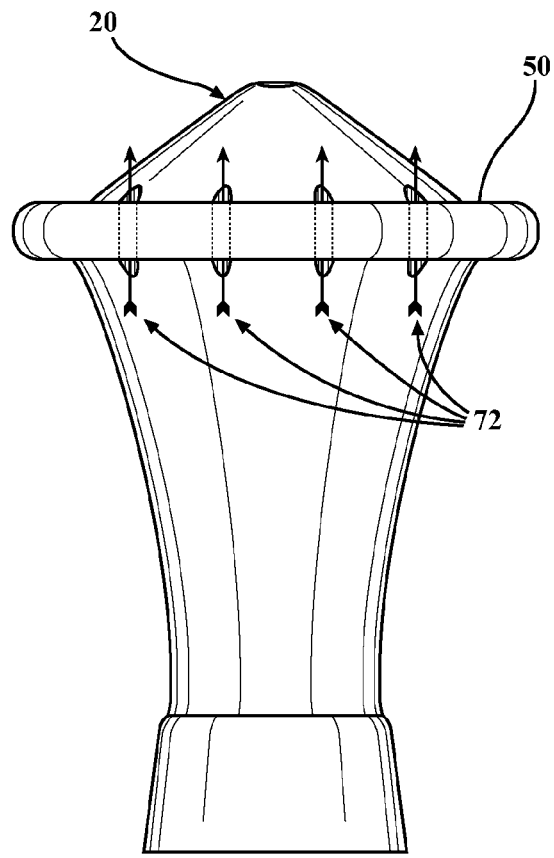
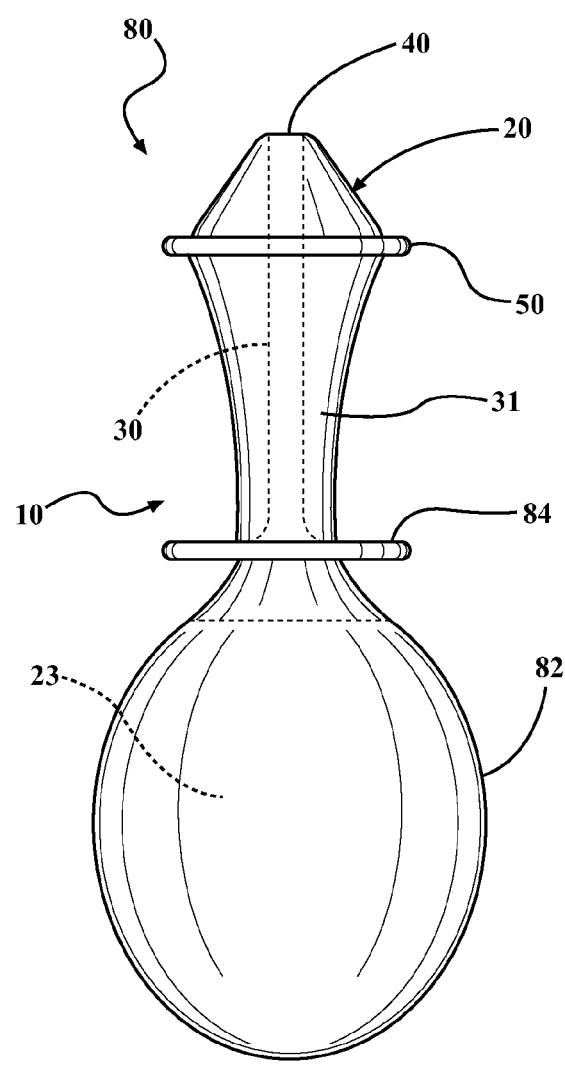
FIG. 6
FIG. 7

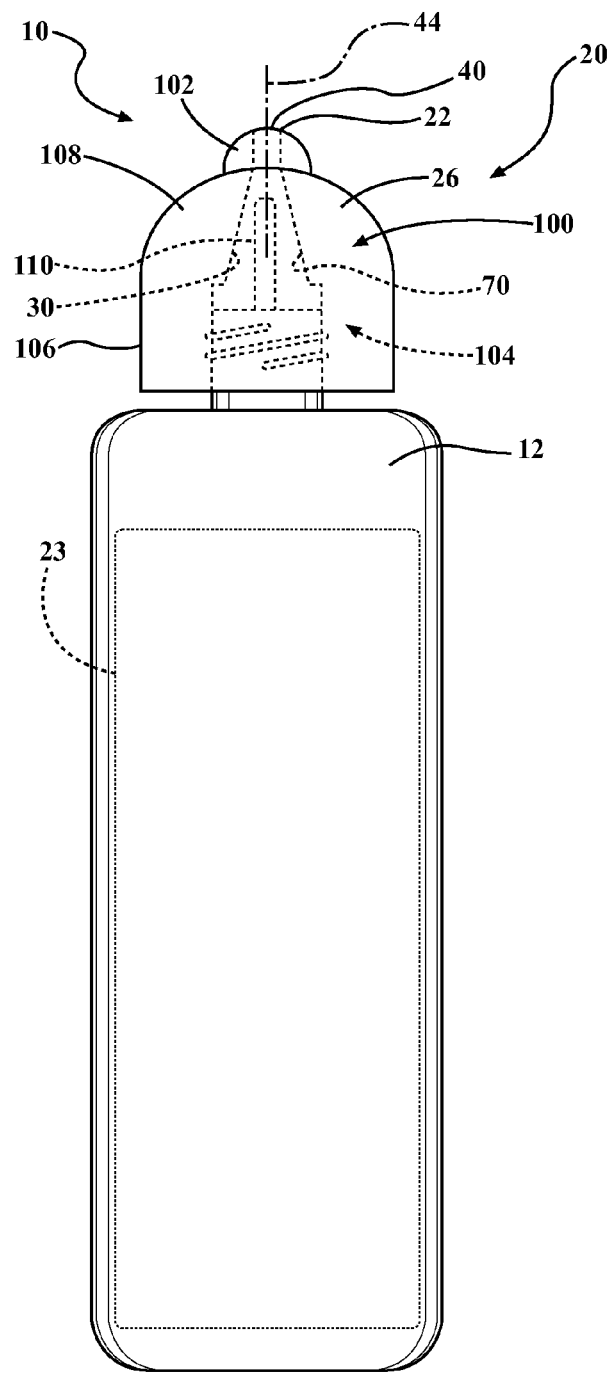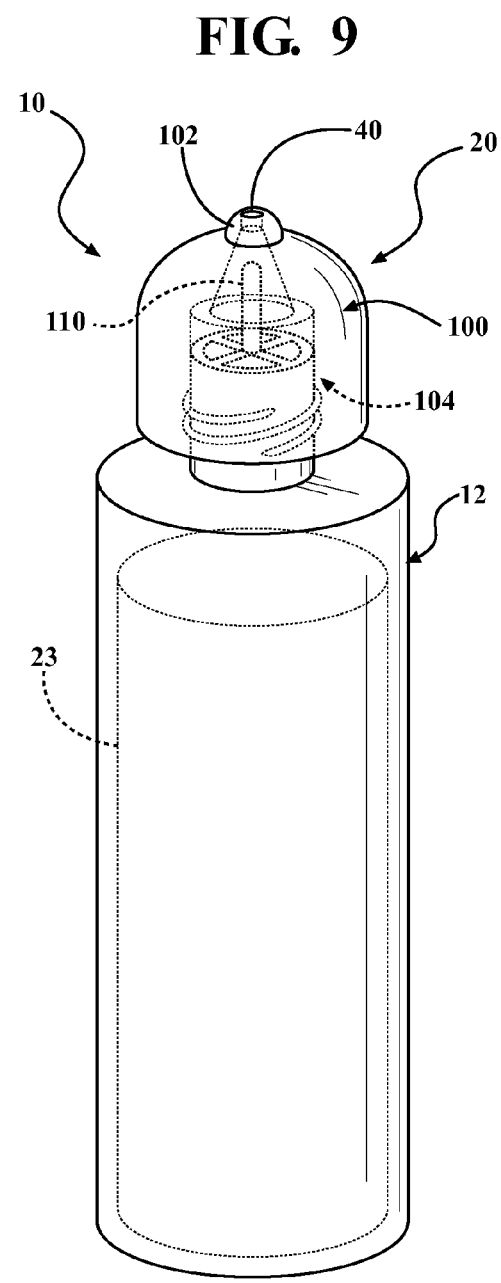

NON-PENETRATING NOZZLE

CROSS REFERENCE TO RELATED APPLICATIONS

The subject patent application claims priority to and all the benefits of International Application No. PCT/US11/038375, filed on May 27, 2011 with the World Intellectual Property Organization, which in turn claims priority to U.S. provisional application No. 61/445,126 filed Feb. 22, 2011 and U.S. provisional application No. 61/349,450 filed May 28, 2010. The entire enclosures of these applications are incorporated herein by reference.

BACKGROUND

1. Field

The inventive concepts relate to a non-penetrating nozzle for delivering a fluid into an orifice of the cavity formed by soft tissue. More specifically, the inventive concepts relate to an enema nozzle or a douche nozzle, which does not penetrate the orifice by creating a seal against the tissue of the orifice while delivering a jet of fluid to cleanse, medicate, stimulate evacuation, or for diagnostic purposes, and the like. The inventive concepts are also applicable for the veterinary medical purposes.

2. Related Art

An enema is a common medical procedure whereby fluid is injected into the rectum of a patient to induce bowel movement. The need for such a procedure typically arises in patients suffering from certain physical ailments in which voluntary bowel control is impaired.

At least one type of device or enema used for such a procedure includes squeeze bottle filled with the fluid intended to induce bowel movement. The squeeze bottle is capped by an applicator nozzle configured to be inserted into the patient's rectum through the anal opening or anus. The applicator nozzle of this type of the related art enema device often causes discomfort and irritation when being inserted.

Disposable enemas for self-application include an enema squeeze bottle filled with the fluid intended to induce bowel movement. This bottle is capped by a long pointed anal insertion fluid delivery nozzle. The nozzle tip is configured to penetrate the anal opening and to be inserted past the exterior and interior sphincter muscles. The fluid filled bottle is squeezed causing the fluid to be jettisoned into the rectal cavity.

The insertion applicator nozzle of the related art enema application devices often causes discomfort and irritation when inserted into the rectum. Extreme care must be taken during the insertion process to avoid injuring the delicate rectal tissue or puncturing existing polyps or hemorrhoids.

Therefore, there is a need for a device, and a method of using the device, that delivers fluid into the rectal cavity by a nozzle that avoids causing discomfort and pain.

SUMMARY

The exemplary embodiments of described herein may address at least the above problems and/or disadvantages and other disadvantages not described above. Also, the exemplary embodiments are not required to overcome the disadvantages described above, and an exemplary embodiment of the present inventive concept may not overcome any of the problems described above.

According to an aspect of an exemplary embodiment, a device administers a fluid from a container into a human cavity or animal cavity, the device including a nozzle configured to be placed in external contact with tissue surrounding an orifice without penetrating the orifice, the nozzle including a discharge opening, through which the fluid is ejected into the human cavity or the animal cavity, a base disposed opposing the discharge opening, and a side wall that extends from the discharge opening towards the base and configured so that the tissue surrounding the orifice conforms to the shape of the side wall so as to form a leaktight seal between the tissue and the orifice; and an interior conduit disposed within the side wall and configured to deliver the fluid from the container to the discharge opening.

According to an aspect of an exemplary embodiment, a nozzle for administering a fluid from a container into a human cavity or animal cavity through an orifice of the cavity is provided. The nozzle includes a base portion for mounting the nozzle to the container; a top face spaced from the base portion; an interior passageway extending between the base portion and the top face along a vertical axis for delivering the fluid from the container to the top face into the human cavity or the animal cavity through the orifice; a rim disposed between the base portion and the top face with the rim projecting radially outward relative to the vertical axis; and a side wall extending between the top face and the rim and having a predetermined configuration for conforming to a tissue surrounding the orifice to seal the orifice during delivery of the fluid from the container into the human cavity or the animal cavity.

According to an aspect of an exemplary embodiment, there is provided an assembly for administering a fluid into a human cavity or animal cavity through an orifice. The assembly includes a container for housing the fluid; a nozzle selectively mounted to the container for delivering the fluid from the container into the human cavity or the animal cavity, the nozzle having a base portion selectively mounted directly to the container, a top face spaced from the base portion, an interior passageway extending between the base portion and the top face along a vertical axis for delivering the fluid from the container to the top face into the human cavity or the animal cavity through the orifice, a rim disposed between the base portion and the top face and projecting radially outward relative to the vertical axis, and a side wall extending between the top face and the rim and having a predetermined configuration for conforming to a tissue surrounding the orifice to seal the orifice during delivery of the fluid from the container into the human cavity or the animal cavity.

According to an aspect of an exemplary embodiment, there is provided a method of administering fluid from a container into a human cavity or an animal cavity through an orifice of the cavity utilizing a nozzle connected to the container, the nozzle having a top face, a radially projecting rim and a side wall extending between the top face and the rim. The method includes pressing the nozzle against the orifice without penetrating the orifice and with sufficient pressure to create a leaktight seal between tissue surrounding the orifice and the side wall of the nozzle, and squeezing the container so as to force the fluid contained in the container to exit the top face in the nozzle and enter the cavity through the orifice.

BRIEF DESCRIPTION OF THE DRAWINGS

The above and/or other aspects will become more apparent by describing certain exemplary embodiments, with reference to the accompanying drawings, in which:

FIG. 6 illustrates a non-penetrating enema nozzle having a barrier ring with release ports according to an exemplary embodiment;

FIG. 7 illustrates a spritz device including a non-penetrating nozzle according to an exemplary embodiment;

FIG. 8 illustrates a bottle with a non-penetrating nozzle according to an exemplary embodiment;

FIG. 9 illustrates a perspective view of a bottle with a non-penetrating nozzle according to an exemplary embodiment;

DESCRIPTION

Figure 1:
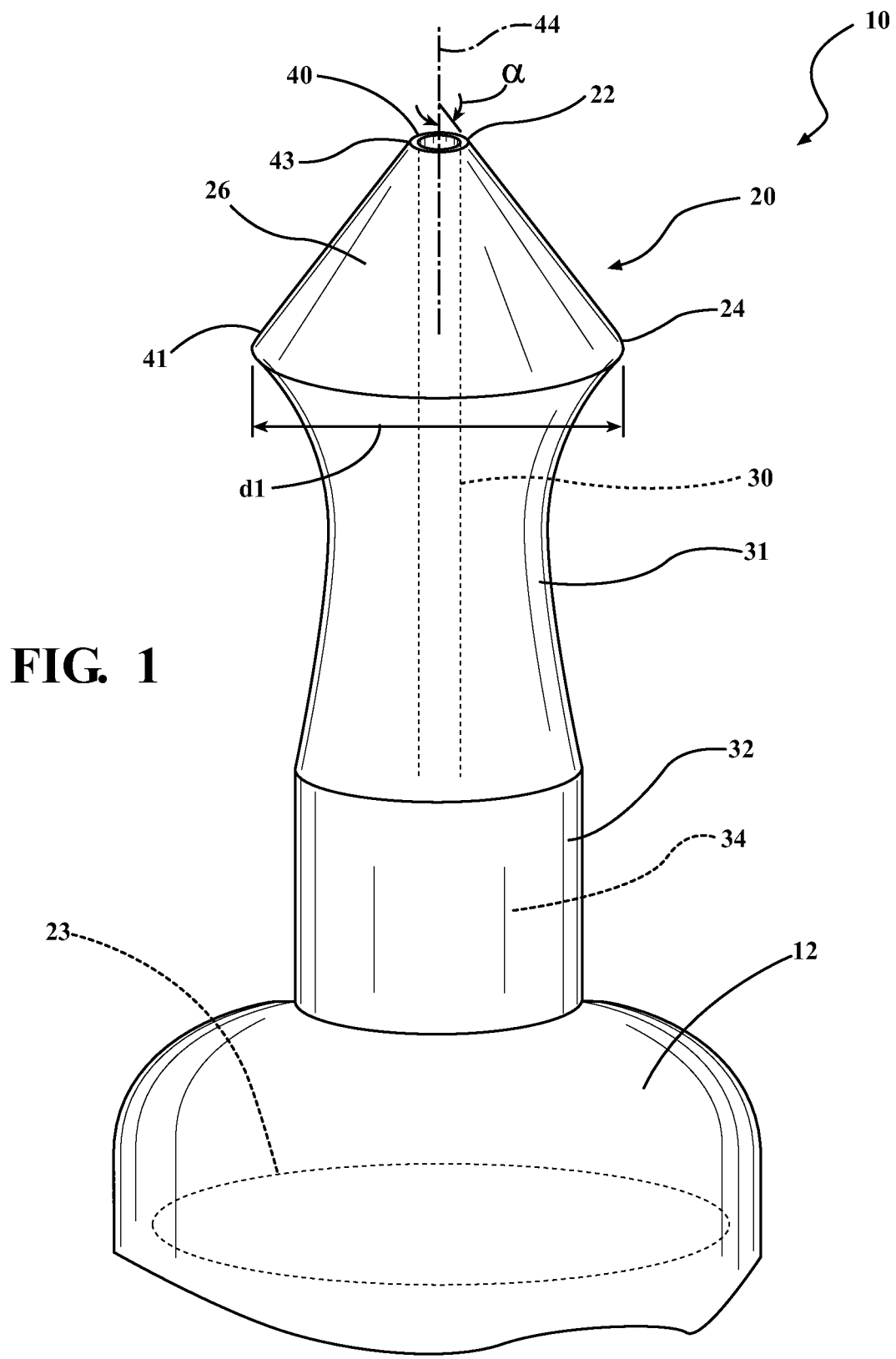
FIG. 1 illustrates a non-penetrating enema nozzle according to an exemplary embodiment.

Certain exemplary embodiments are described in greater detail below with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be carried out without those specifically defined matters. Also, well-known functions or constructions are not described in detail since they would obscure the invention with unnecessary detail.

Exemplary embodiments provide a flow-through enema nozzle that does not penetrate the anus or does not pass the exterior or interior sphincter muscles, but instead is pressed against the anal opening while it delivers a jet of liquid from a liquid filled squeeze bottle into the anus and rectal cavity for cleansing, stimulating evacuation, or for diagnostic purposes.

In accordance with one aspect of the disclosure, a non anus-penetrating enema delivery nozzle is disclosed which is made of Food and Drug Administration (FDA) approved materials. Meeting FDA requirements, exemplary embodiments provide a hard or flexible plastic non-penetrating fluid delivery enema nozzle attached to a flexible plastic squeeze bottle. The non-penetrating nozzle may also have a smaller shallow dome shaped nipple on the top of the nozzle that will make locating the center point of the anus easier as resistance will be felt when the nipple slides into the depression of the anal opening Once the anal opening is located, the bottle can be pressed gently against the anus whereby the tissue surrounding the anal opening will conform to the non-penetrating nozzle creating a seal that will make the anal opening the path of least resistance for the fluid when the bottle is squeezed. By maintaining the non-penetrating nozzle's gentle pressure against the anus while squeezing the bottle, the area around the anal opening will remain conformed to the non-penetrating nozzle maintaining the necessary seal that will allow the water to jettison into the anal opening past the exterior and interior sphincter muscles and into the rectal cavity. Fluid will be delivered to the same destination as anal-penetrating nozzle enemas without the common penetration discomfort and without the danger of injuring delicate rectal tissue.

Exemplary embodiments also provide a flow-through non-invasive enema or douche nozzle of various possible non-penetrating ergonomic shapes that does not penetrate the anus or vagina but instead is pressed against the anal or vaginal opening to create a seal while it delivers an appropriate amount of prescribed liquid from an attached liquid-filled squeeze bottle, squeeze bulb of any shape or capacity or any appropriate fluid container into the anus and rectal cavity and/or vagina for cleansing, pre-sexual penetration lubrication, pre-bowel movement rectal and/or hemorrhoid lubrication, rectal delivery of medication or laxatives, to stimulate evacuation, or for pre or post-diagnostic purposes. For purposes of clarity, the following description is made regarding primarily in the context of an enema application in accordance with the invention, however, the same inventive features may be used as a means of a non-penetrating fluid delivery nozzle into the vagina or uterine cavity as well.

In accordance with one aspect of the disclosure, a non anus-invasive or non-penetrating enema delivery nozzle is disclosed which is made of Food and Drug Administration approved materials. Exemplary embodiments provide a hard or flexible non-penetrating fluid delivery enema nozzle of any appropriately ergonomic shape attached to, screwed-on to, or part of a one-piece flexible plastic squeeze bottle or squeeze bulb of any shape or capacity or a pre-pressurized or pump container. Although any non-penetrating shaped nozzle can be used, a featured nozzle in this disclosure is cone shaped. The cone shape has primary advantages in that it allows the smaller diameter tip of the cone to more easily locate the anal opening as it will be felt when the smaller cone tip slides into anal opening depression. The smooth flaring diameter of the cone shape also creates a consistent surface on which the soft tissue of any size anal opening will conform creating the necessary even-pressure tissue-to-cap seal for the fluid to be effectively delivered absent of or with minimal leakage and with minimum discomfort. Once the anal opening is located, the cone shaped nozzle capped bottle or bulb is pressed gently toward the anus whereby the tissue surrounding the anal opening will conform to the cone-nozzle creating a seal that will make the anal opening the path of least resistance for the ejected fluid while the bottle or bulb is being squeezed. Fluid will be delivered to the same destination as anal-penetrating nozzle enemas without the common penetration discomfort and without the danger of injuring delicate rectal or hemorrhoid tissue. The non-penetrating nozzle also eliminates the possibility of the nozzle opening become plugged by fecal matter as can happen with the current inserted nozzle tips. Additionally, the nozzle may or may not have an insertion barrier surface or ring surrounding the base of the cone-nozzle that will provide extra resistance preventing the nozzle from accidentally being inserted past the exterior sphincter muscle. Vacuum release ports or spaces may or may not be arranged around the cap such as the widest dimension of the cap to allow outside air to flow in past the nozzle during extraction if the entire cap is accidentally inserted into the anus, thus preventing a vacuum that can potentially cause damage to tissue during extraction.

Also disclosed is a daily pre-bowel movement lubricating spritz application of the non-penetrating nozzle that is designed to eject a smaller amount of sterilized distilled water or appropriate lubricating fluid or the like into the anus via a squeeze-bulb. Such applications are primarily to reduce hemorrhoid tissue irritation from passing fecal matter and, therefore, promote natural healing of delicate, pre-hemorrhoid and hemorrhoid rectal tissue. The introduction of a lubricating spritz into the rectum prior to fecal evacuation will also reduce the need to strain during a bowel movement which can further exacerbate hemorrhoid inflammation. The pre-lubricated tissue will also promote a more complete evacuation of fecal matter that could otherwise leave an irritating fecal film on drier, delicate rectal and hemorrhoid tissue. The same application may also be used for pre-sexual anal or vaginal penetration lubrication.

According to exemplary embodiments, a non-penetrating enema and/or douche nozzle provides for, among other things:

a. a means for safely delivering enema fluid into the rectal cavity without using a penetrating enema nozzle tip.

b. a means for safely delivering douche fluid into the vaginal cavity without using a penetrating douche nozzle tip.

c. a cone-shaped, dome-shaped, or any other effectively shaped non-penetrating enema nozzle tip that will jet enema fluid into the rectal cavity without risking injury to delicate anal tissue that is common with anus-penetrating pointed enema nozzles.

d. a cone-shaped, dome-shaped, or any other effectively shaped non-penetrating douche nozzle tip that will jet cleansing fluid into the vaginal cavity without rising injury to delicate vaginal tissue.

e. easy positioning by the smaller diameter tip of the cone shape or dome shape nipple that will act as an indicator for users to be certain when the nozzle tip is properly positioned at the anal orifice.

f. easy positioning by the smaller diameter tip of the cone shape or a dome shape nozzle will act as an indicator for users to be certain when the nozzle tip is positioned over the vaginal opening.

g. an additional daily pre-bowel movement lubricating spritz application using the non-penetrating tip and a squeeze bulb to reduce fecal abrasion to delicate rectal and hemorrhoid tissue and provide for a more complete fecal evacuation in order to minimize remaining fecal matter that can further irritate and prevent natural healing of hemorrhoid or other inflamed rectal tissue.

h. an additional pre-sexual intimacy vaginal lubricating or freshening spritz application of the non-penetrating tip and a squeeze bulb.

i. Reduction in the urge to strain during a bowl movement which can further exacerbate hemorrhoid thrombosis and prolapse.

j. Elimination of discomfort and potential injury that can occur with penetrating enema nozzles.

k. optional use of a lubricant on the nozzle to aid in smoother and exact locating of the anal orifice during pre-application positioning.

l. optional vacuum release ports openings or spaces to provide for safer extraction should accidental insertion of the entire tip occur.

m. the non-penetrating nozzle that alleviates the problem of fecal plugging of the tip that is common with penetrating tips.

n. a strong water pressure jet velocity created by the Bernoulli Principle by an interior narrowing or cone-shaped conduit inside the nozzle through which fluid passes to inject the fluid into the rectal cavity without penetrating the anal orifice.

With reference to FIG. 1, a device 10 may be used by a person to self-administer the enema or another fluid by squeezing a container 12 filled with fluid 23 such as the fluid for an enema or a douche.

For example, a non-penetrating nozzle 20 may deliver enema fluids to one of the rectal cavity and the uterine cavity. While the non-penetrating enema nozzle is depicted in FIG. 1 as having a cone shape, it must be understood that the non-penetrating nozzle may be of other shapes consistent with creating the proper seal in the human cavity, such as at the anus and the exterior sphincter for the non-penetrating nozzle 20 to deliver fluid 23 to the rectal cavity, or at applicable tissue of other human cavity, as for example, the uterine cavity.

The nozzle 20 includes an end face or a top face 22 which is configured to be placed in external contact with an orifice of the human cavity to eject the fluid into the human cavity, as described in greater detail below.

The nozzle 20 includes a base or a rim 24 which is disposed opposing the end face 22, and a side wall 26 which extends from the end face 22 toward the base 24 and conforms to a tissue surrounding the orifice of the human cavity to seal the orifice. The base 24 may have, for example, a diameter d1 ranging from approximately 15 mm to approximately 20 mm.

An interior port, interior conduit, or interior passageway 30 is disposed within the side wall 26 and delivers the fluid from the container 12 to the end face 22. An elongated portion 31 surrounds the interior port 30 and extends down from the base 24 of the nozzle 20 toward the container 12. A base portion 32 matches with a feeding portion 34 of the container 12.

The end face 22 has a discharge opening 40 which is formed in substantially a center of the end face 22 and is adapted to receive the fluid from a lower end of the interior port 30. The interior port 30 may be positioned within the discharge opening 40 such that the end of the interior port 30 is substantially flush with the end face 22 or may be positioned at a distance from the end face 22.

The side wall 26 may be a conical side wall and may include substantially straight outer surface 41 which extends from the base 24 to an outer edge 43 of the end face 22. The side wall 26 is positioned at an angle α with respect to a vertical axis 44 of the nozzle 20 so that the substantially straight surface 41 of the side wall 26 forms a cone-shaped nozzle. The straight surface of the side wall 26 of the cone-shaped nozzle exerts an even pressure on the tissue surrounding the anal orifice.

The angle α may be from approximately 30 degrees to approximately 60 degrees. In one embodiment, the angle α may be from approximately 40 degrees to approximately 55 degrees. In another embodiment, the angle α may be from approximately 45 degrees to approximately 50 degrees. Nozzles may be formed with angles outside these ranges to varying lesser degree of performance in terms of sealing and comfort.

In one embodiment, the end face 22 may include multiple discharge openings. The non-penetrating nozzle 20 may be screwed on or affixed by other means to the container 12 or to any other appropriate fluid supply source.

The non-penetrating nozzle 20 may be manufactured in different sizes and lengths to accommodate the age and size of the recipient.

Figure 2:
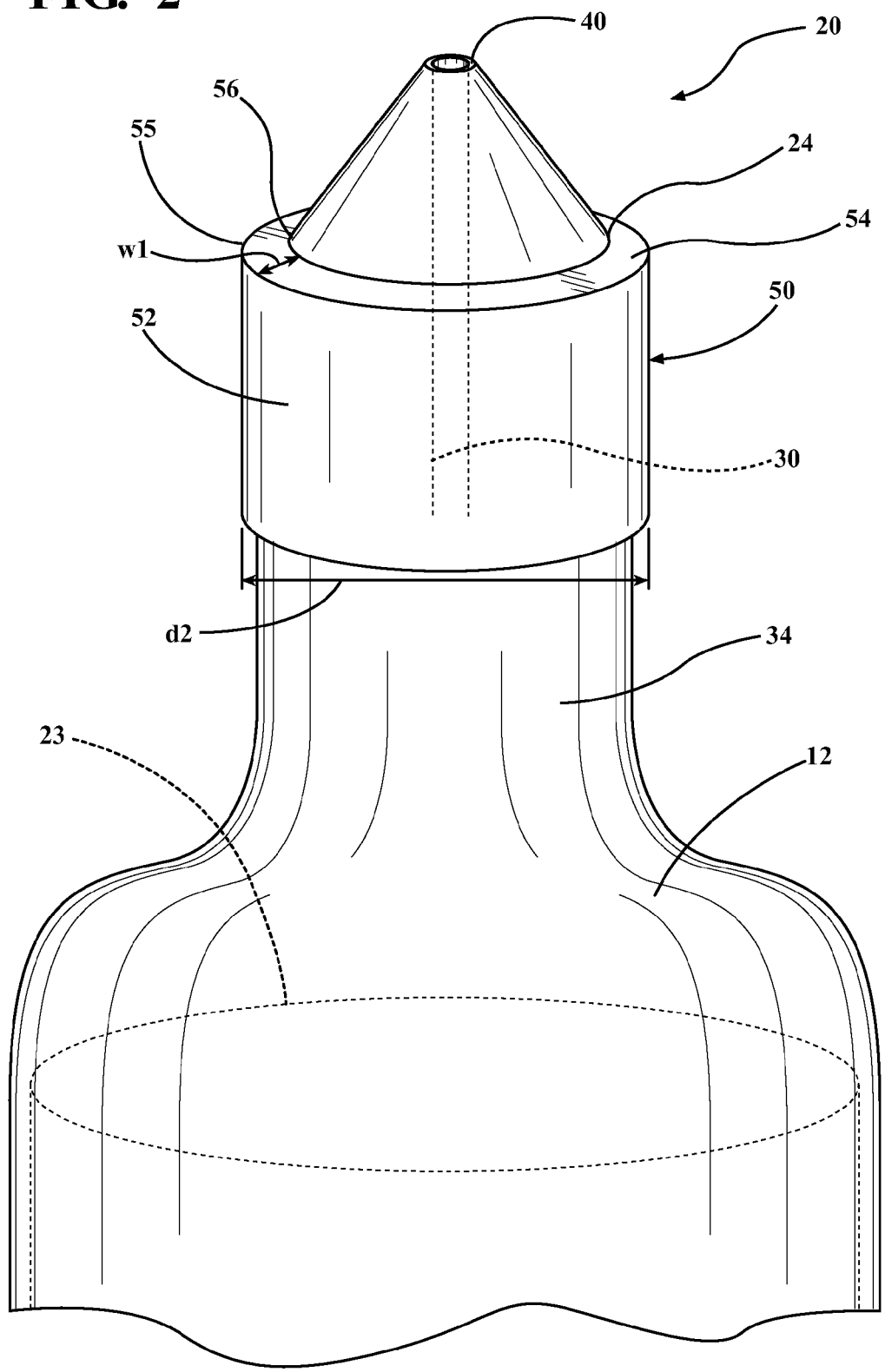
FIG. 2 illustrates a non-penetrating enema nozzle with a barrier ring according to an exemplary embodiment.

Referring to FIG. 2, the non-penetrating nozzle 20 may include a barrier shown in this example as an insertion-barrier ring 50 disposed at the base 24 of the nozzle 20. The insertion-barrier ring 50 is configured to be disposed outside of the orifice of the human cavity while the nozzle 20 seals the orifice to reduce the risk of the nozzle being inserted into the anus. The insertion-barrier ring 50 extends from the base 24 of the nozzle 20 and includes a circumferential outer surface 52 which surrounds the interior port 30, thus forming a cylinder-like structure. The insertion-barrier ring 50 may have a diameter d2, for example, from approximately 20 mm to approximately 25 mm.

A barrier hip 54 is disposed between an outer edge 55 of the circumferential outer surface 52 and an outer edge 56 of the base 24 of the nozzle 20. To provide an adequate barrier against insertion into the anus, the hip 54 may have a width w1, for example, from approximately 2 mm to approximately 5 mm. In one embodiment, the hip 54 may have the width w1 from approximately 3 mm to approximately 4 mm.

In one embodiment, a diameter of the insertion-barrier ring at the barrier hip 54 may be the same diameter as the screw cap portion of the tip of the container. This allows the cap to be molded and ejected from the mold using a one cavity die, whereas the use of any protruding or intruding shapes in the design may require a more complex two cavity die that could produce undesirable die seams on the cap.

Figure 3:
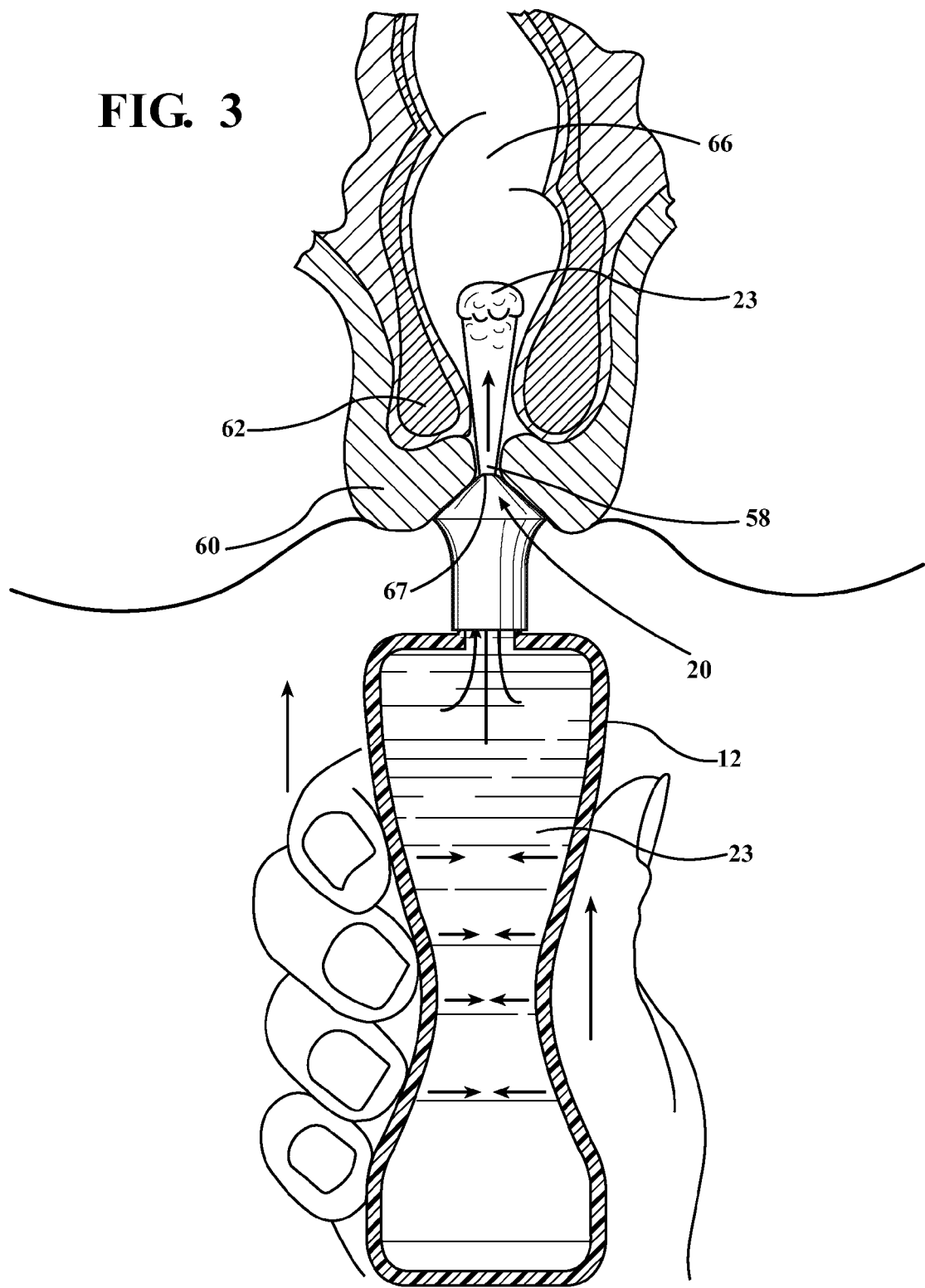
FIG. 3 illustrates a non-penetrating enema nozzle pressed against an external anal opening according to an exemplary embodiment.
Figure 4:
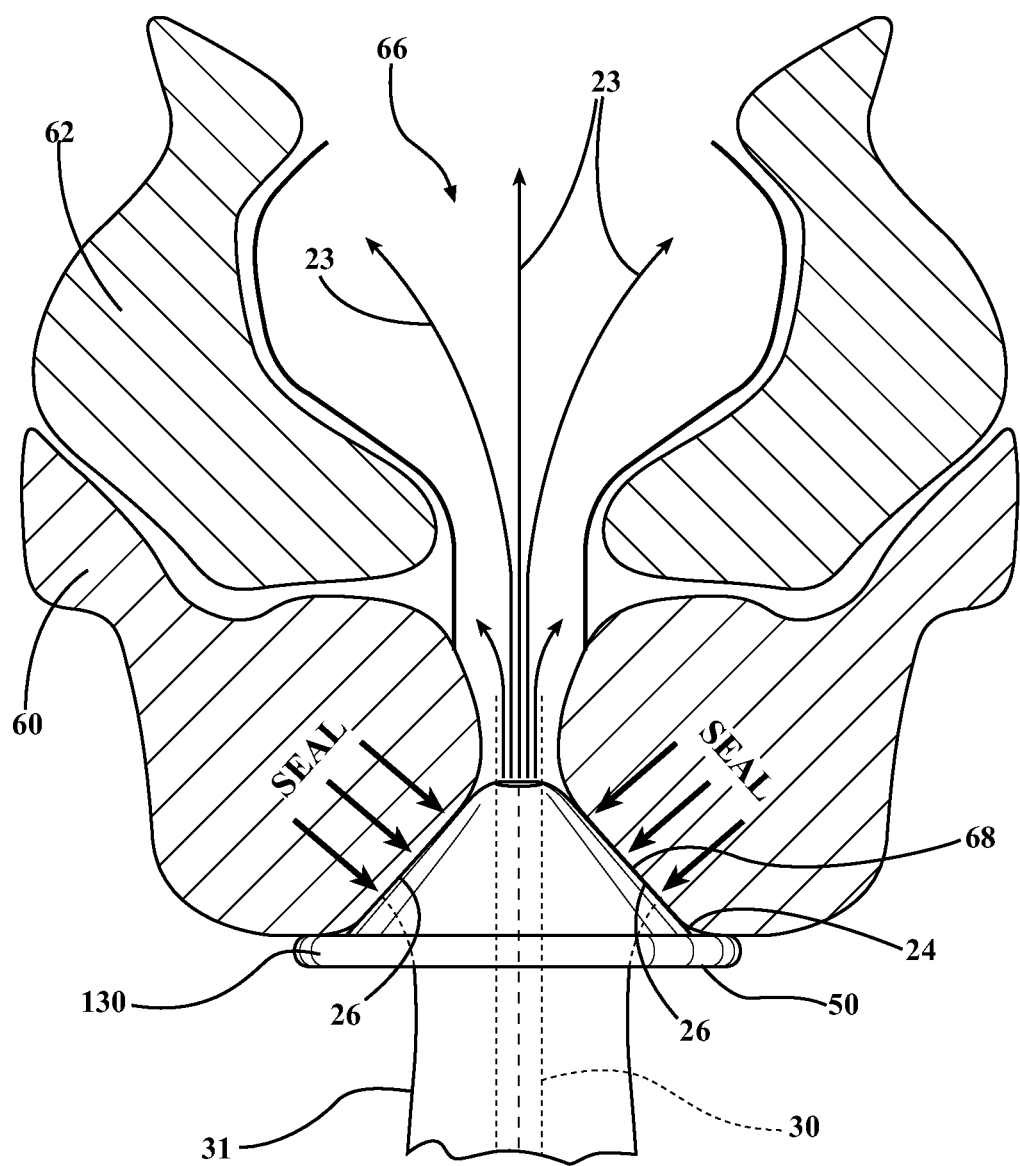
FIG. 4 is a close-up view illustrating a non-penetrating nozzle pressed against an external anal opening according to an exemplary embodiment.
Figure 5:
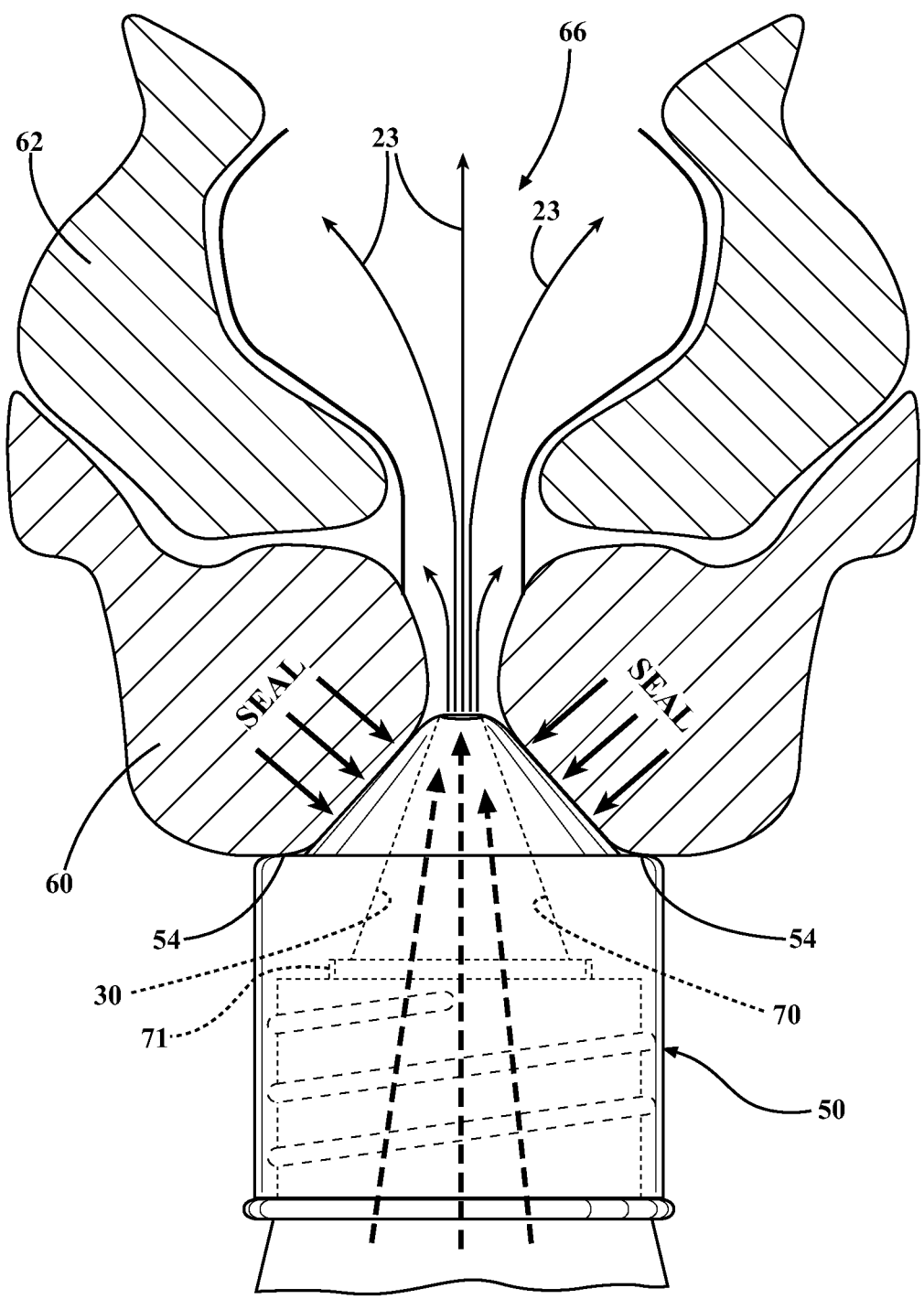
FIG. 5 illustrates another close-up view illustrating a non-penetrating nozzle directing an ejected fluid according to an exemplary embodiment.

Referring to FIGS. 3, 4, and 5, the non-penetrating nozzle 20 is shown pressed against, but not into, an external orifice 58, such as, for example, an anal orifice, creating a consistent and fluid tight seal that allows the enema fluid 23 to be jetted on to and past the exterior sphincter muscles 60 and interior sphincter muscles 62 and into the rectal cavity 66 when the fluid 23 is ejected from the container 12.

When a rounded tip 67 of the nozzle 20 is resting on the external orifice 58 and/or the tissue of the exterior sphincter muscles 60, the end face 22 of the nozzle 20 may be pressed against, but not into the anus and exterior sphincter muscles 60, by using gentle additional pressure. The external tissue surface of the exterior sphincter muscles 60 conforms to the cone shape of the side wall 26 of the nozzle 20 creating a liquid tight and even seal. The even seal made possible due to the cone shape design ensures that there are no focused pressure points that can cause discomfort or injury and that the minimum amount of pressure is applied to create the liquid tight seal. Additionally, the cone shape design inherently adapts to different size external orifices 58, such that one cone-shaped nozzle size, for example, can be used for adults and children.

When the seal between the exterior sphincter muscles 60 and the nozzle 20 is achieved, the container 12 is squeezed and the enema fluid 23 is jetted through the interior port 30 inside the nozzle 20 and exits through the discharge opening 40 at an adequate velocity into and past the exterior sphincter muscles 60 and interior sphincter muscles 62 and is delivered into the rectal cavity 66 and surrounding tissue.

The narrower rounded point on the cone nozzle tip is designed to come to rest on the anal orifice at the exterior sphincter, thus assisting the user, whether administering the enema to oneself or to another, by indicating through slight resistance while sliding the nozzle into position when the cone nozzle tip is centered at the anal orifice/external sphincter soft tissue depression. The entire cone nozzle tip may be optionally pre-lubricated.

FIG. 4 illustrates in greater detail how the cone-shaped non-penetrating tip creates a consistent and effective seal between the side wall 26 of the nozzle 20 and the exterior sphincter tissue 68 while at the same time affecting a slight opening and relaxation of the anus for the fluid to pass more easily without penetration.

In an illustrated example, the insertion-barrier ring 50, preferably with a rounded edge for comfort and safety, may be disposed between the base 24 of the nozzle and the elongated portion 31 outside the orifice while the nozzle seals the orifice. The insertion-barrier ring 50 provides extra resistance to help to prevent over-insertion of the nozzle 20. The insertion-barrier ring 50 has rounded side edges 130, for user's comfort.

FIG. 5 illustrates the interior port 30 having a cone-shaped interior port 70 directing the ejected fluid at an increased velocity due to the Bernoulli Effect. The insertion-barrier ring 50 includes a hip 54 that allows the cap to be manufactured using a single-cavity die that eliminates the seam that is common using a two-cavity die. FIG. 5 also shows the placement of a reflux-valve 71 that helps to prevent the fluid from being ejected prior to positioning and also prevents a backflow of air and fluid into the container prior to a second squeeze of the squeeze container.

Referring to FIG. 6, the nozzle may have release ports or spaces for vacuum release in the barrier, such as release ports 72 on the insertion-barrier ring 50. The release ports 72 allow the entire nozzle 20 to be extracted after accidental insertion of the nozzle 20 and insertion ring 50 without potentially dangerous vacuum resistance during extraction.

In another embodiment, the release ports 72 may be configured differently to achieve the same vacuum release properties and may be disposed in the nozzle, such as in the side wall of the nozzle 20 which includes the insertion-barrier ring 50. In yet another embodiment, the release ports 72 may be disposed in the nozzle 20 which does not include the insertion-barrier ring 50.

Accordingly, the vacuum release ports may be configured at the base of the cone or where the cone meets the optional insertion-barrier ring. In the event of accidental insertion of the entire nozzle and insertion-barrier ring, the vacuum release ports allow outside air to flow in past the tip during extraction from the rectum thus neutralizing any potentially dangerous vacuum that could prevent safe extraction. The vacuum release ports may be configured to have various air-flow ports designs that achieve the same vacuum release properties.

FIG. 7 illustrates an example of the device 10 including a daily spritz 80 including a non-penetrating nozzle 20 and a squeeze bulb 82. For example, the nozzle 20 and the squeeze bulb 82 may be embodied in a one-piece molded configuration. A circular protrusion type ring 84 is disposed between the elongated portion 31 and the squeeze bulb 82, to assist the user in holding and squeezing the bulb 82.

Referring to FIGS. 8 and 9, a non-penetrating nozzle 20 may be a dome-shaped flow-through enema nozzle that does not penetrate the anus but instead is pressed against the anal orifice while it delivers a jet of fluid from a fluid filled squeeze bottle into the anus and rectal cavity for cleansing, or to stimulate evacuation, or for diagnostic purposes. The entire nozzle 20 may be optionally pre-lubricated. The dome nozzle may be manufactured in different sizes to accommodate the age and size of the recipient.

The non-penetrating nozzle 20 includes the side wall 26 including a dome structure 100 shaped as a dome and converging at the end face 22. The side wall 26 surrounds the interior port 30 and the discharge opening 40 may be located in the end face 22, similar to exemplary embodiments described above.

Optionally, the side wall 26 may include a nipple 102 disposed on the dome structure 100, which can assist in properly locating the nozzle at the opening of the human cavity. The end face 22 may be disposed on the nipple 102, for the fluid to be delivered into the human cavity. A first portion 106 of the dome structure 100 is proximate the container and extends substantially in parallel with the vertical axis 44. A second portion 108 of the dome structure 100 has arcuate shape and extends from the first portion 106 to converge at the end face 22 or at the nipple 102 as a convex or a dome.

While the dome-shaped non-penetrating nozzle 20 is depicted as having a self-sealing twist close and seal feature 104 with an interior plug 110 affixed to the container 12, it is to be understood that the twist close and seal feature 104 is not germane to the functionality of the device because the container 12 may have a tamper resistant removable fluid seal on the container opening instead.

Figure 10:
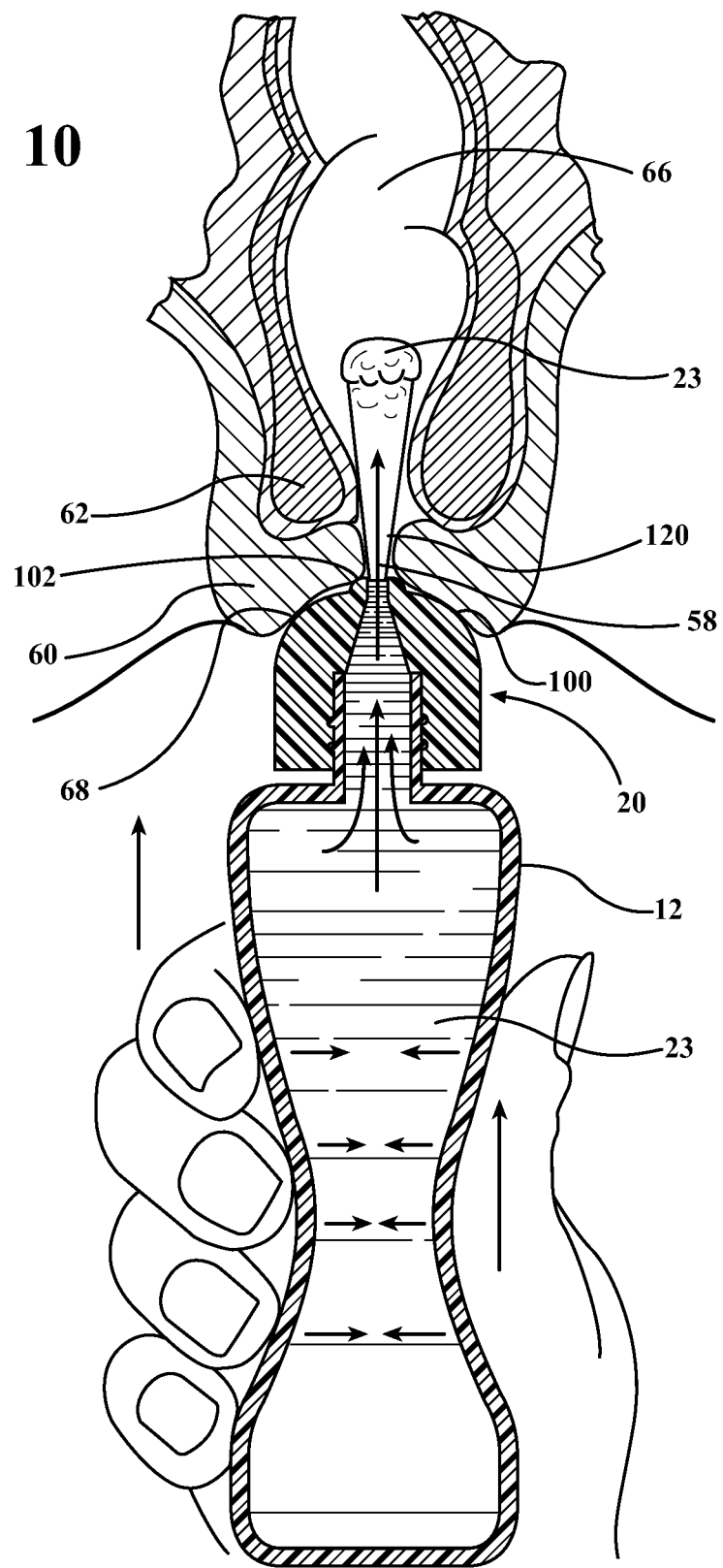
FIG. 10 illustrates a non-penetrating enema nozzle pressed against the external anal opening according to an exemplary embodiment.

Referring to FIG. 10, the nipple 102 on the dome structure 100 comes to rest on the orifice 58 thus assisting the user, whether administering the enema to oneself or to another, by indicating through slight resistance when the nozzle 20 is centered at the anal orifice 58. The non-penetrating dome-shaped enema nozzle is pressed against, but not into, the external anal orifice creating a seal that allows the enema fluid to be jettisoned past the exterior and interior sphincter muscles 60, 62 and into the rectal cavity 66 when the container is squeezed.

When the nipple 102 is resting on the orifice 58, the end surface 22 and the side wall 26 are pressed against the orifice 58 and the tissue 68 of the exterior sphincter muscles 60 by using gentle additional pressure. The surfaces of the tissue 68 of the exterior sphincter muscles 60 conform to the shape of the nipple 102 and the dome structure 100 of the nozzle 20, thus creating a seal.

When the seal between the exterior sphincter muscles 60 and the nozzle 20 is achieved, the container 12 is squeezed and the enema fluid 23 is jettisoned using the Bernoulli Principle created through the reduced cone-shaped interior port 70 inside the nozzle 20 and exits through the discharge opening 40 or discharge openings on the end face 22 at adequate velocity into and past the exterior sphincter muscles 60 (indicated by a reference numeral 120) and interior sphincter muscles 62 and delivered into the rectal cavity 66.

Figure 11:
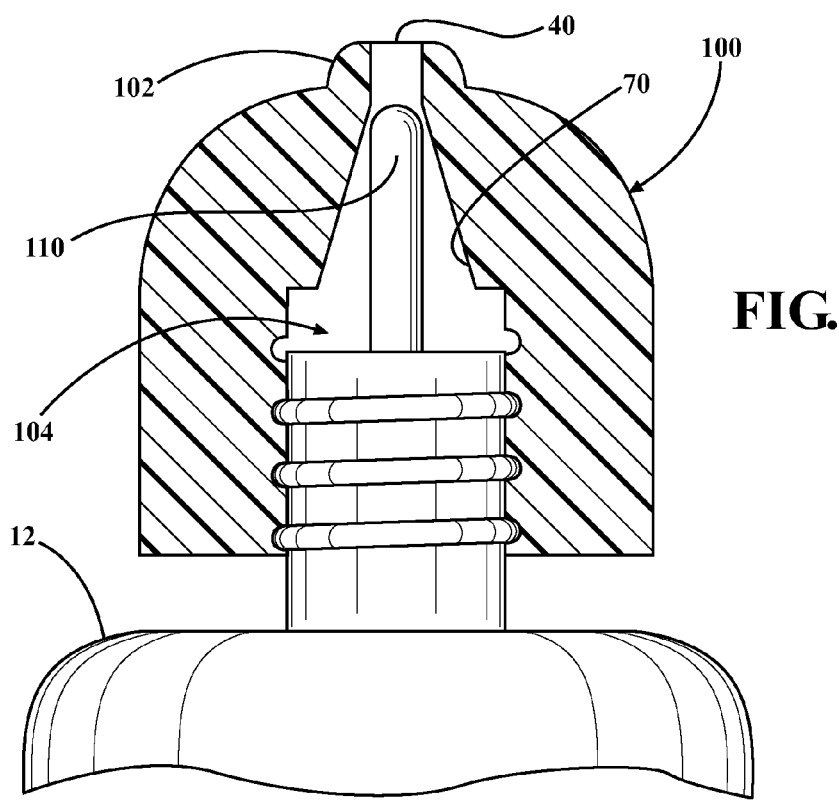
FIG. 11 illustrates an open position of a nozzle using a twist close-and-seal stationary interior nozzle plug according to an exemplary embodiment.
Figure 12:
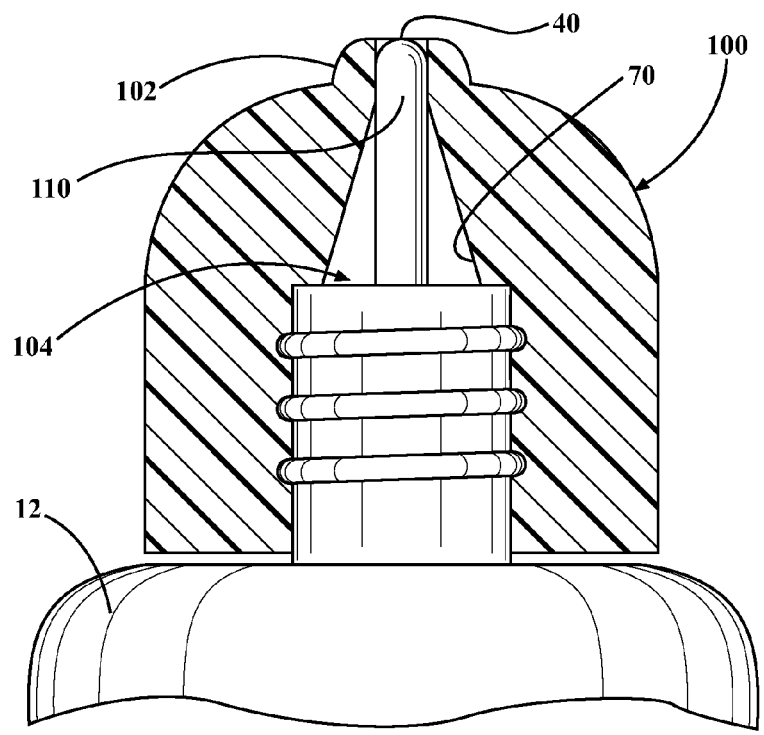
FIG. 12 illustrates a closed position of a nozzle using a twist close-and-seal stationary interior nozzle plug according to an exemplary embodiment.

With reference to FIGS. 11 and 12, the non-penetrating nozzle 20 may include a twist close and seal feature 104. The cap may be screwed on to a squeeze bottle that holds the fluid for the enema.

FIG. 11 shows a cross-section close-up of the dome-shaped nozzle in the open position if it employs an optional twist close-and-seal stationary interior nozzle plug 110.

FIG. 12 shows a cross-section close-up of the dome-shaped nozzle in the closed position if it employs and optional twist close-and-seal stationary interior nozzle plug 110.

Figure 13A:
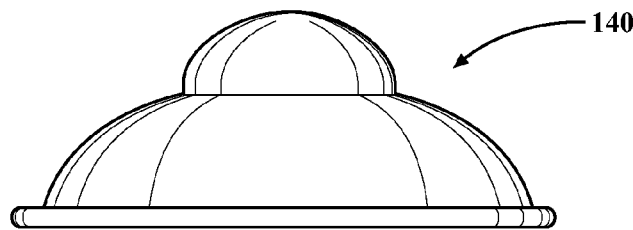
FIGS. 13A and 13B illustrate removable caps for a nozzle according to an exemplary 15 embodiment.
Figure 13B:
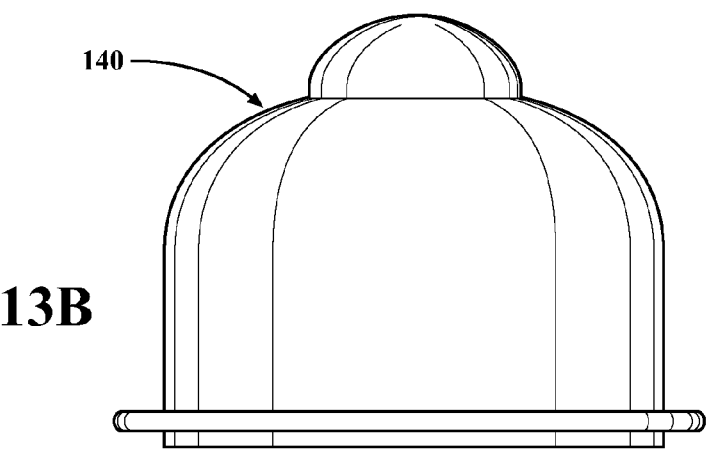
Figure 14:
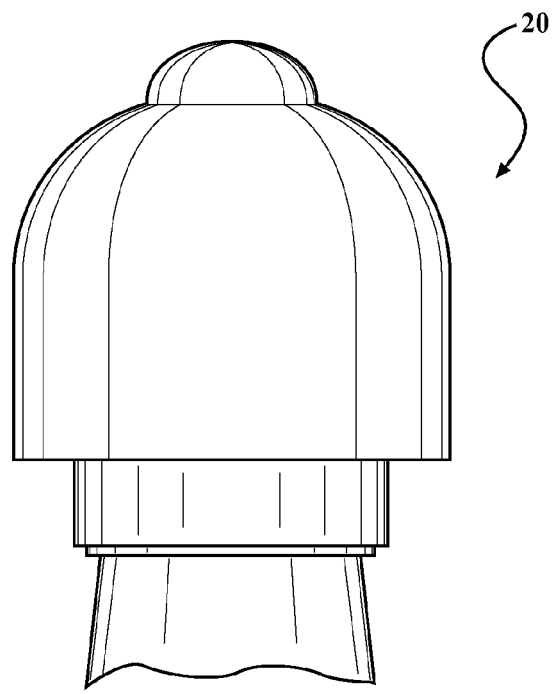
FIGS. 14, 15, 16, 17, 18, 19, 20, 21, 22, 23, 24, 25, 26, 27 28, and 29 illustrate side views of non-penetrating nozzles according to exemplary embodiments.
Figure 15:
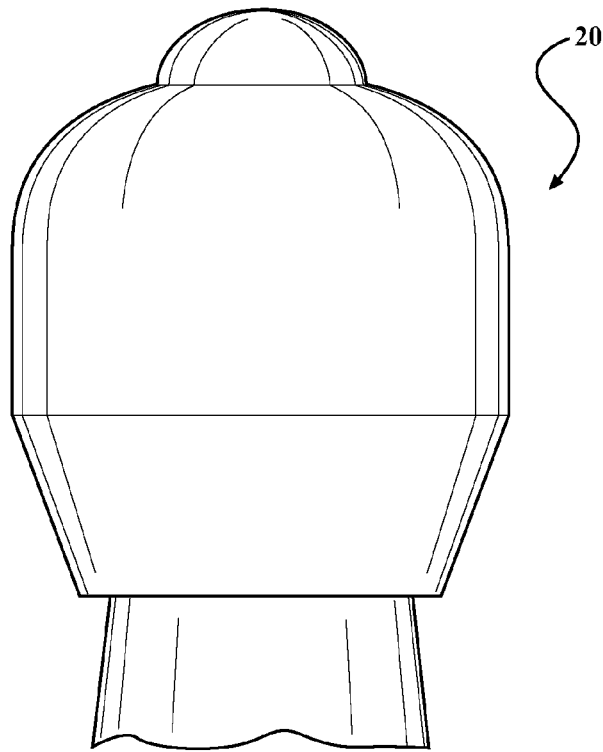
Figure 16:
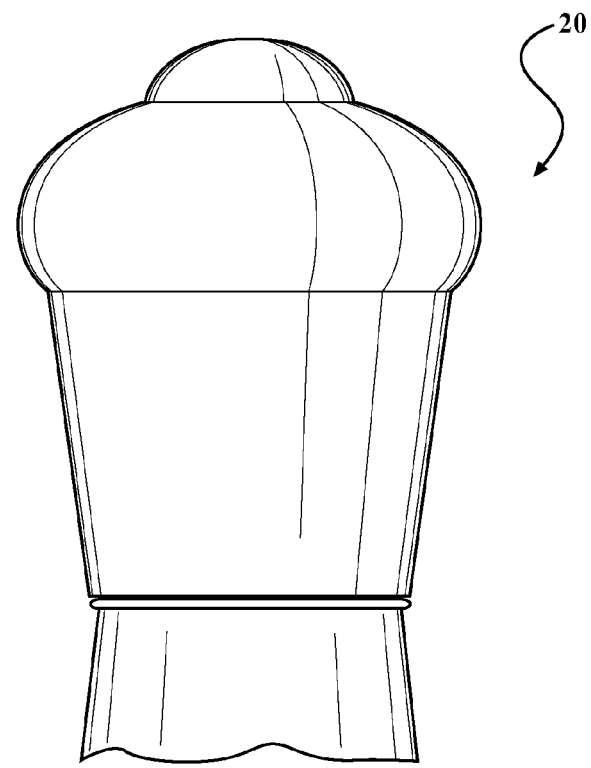
Figure 17:
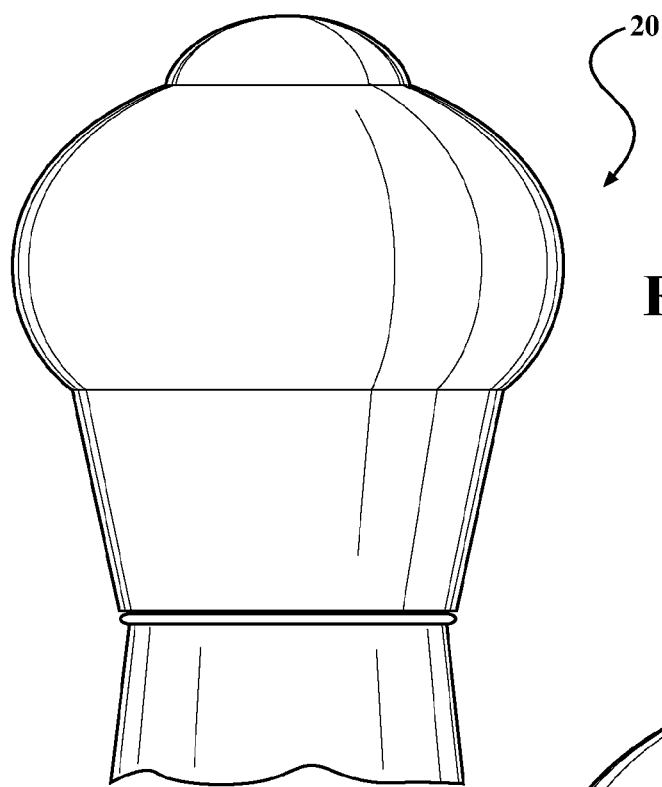
Figure 18:
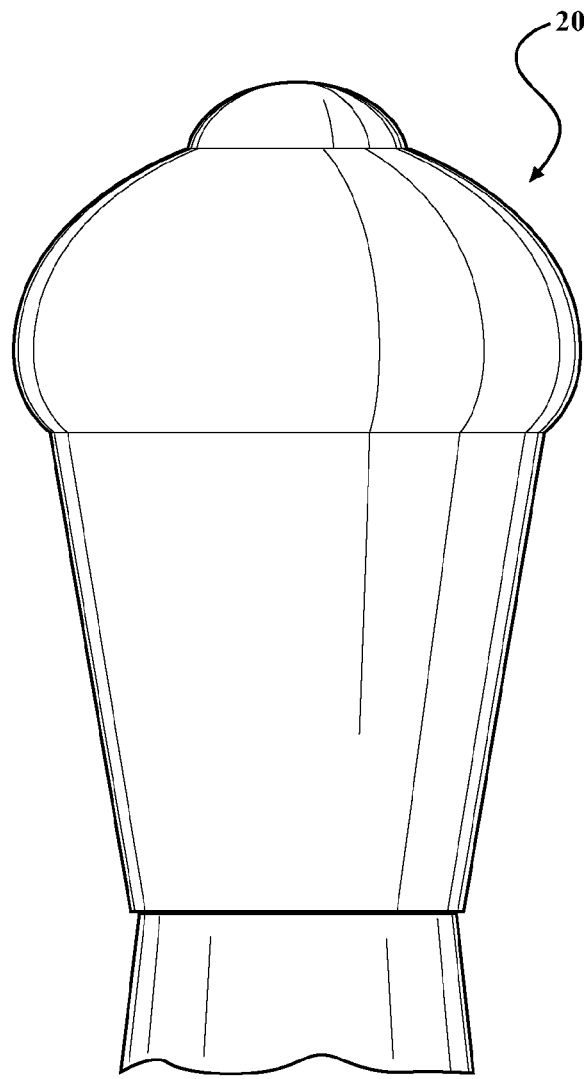
Figure 19:
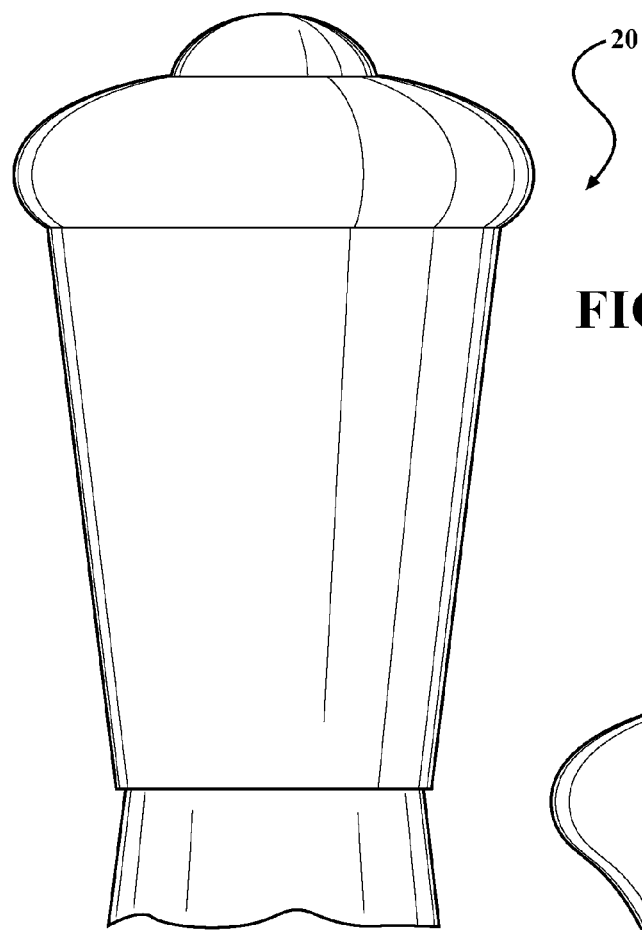
Figure 20:
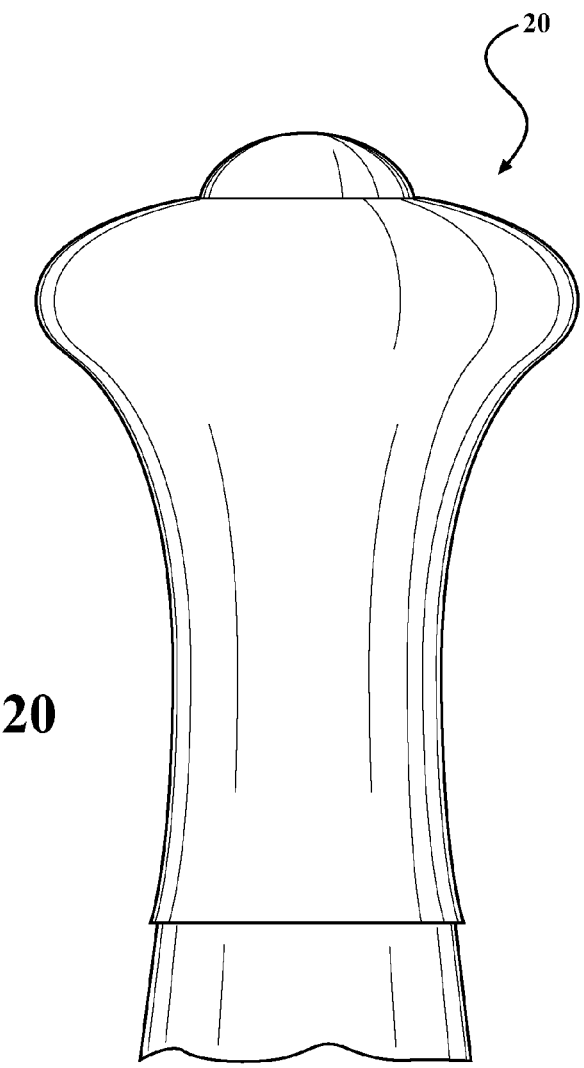

FIGS. 13A and 13B illustrate examples of a removable cap 140 for use with the nozzle 20.

FIGS. 14, 15, 16, 17, 18, 19, 20, 21, 22, 23, 24, 25, 26, 27, 28, and 29 illustrate side views of non-penetrating nozzles 20.

Figure 21:
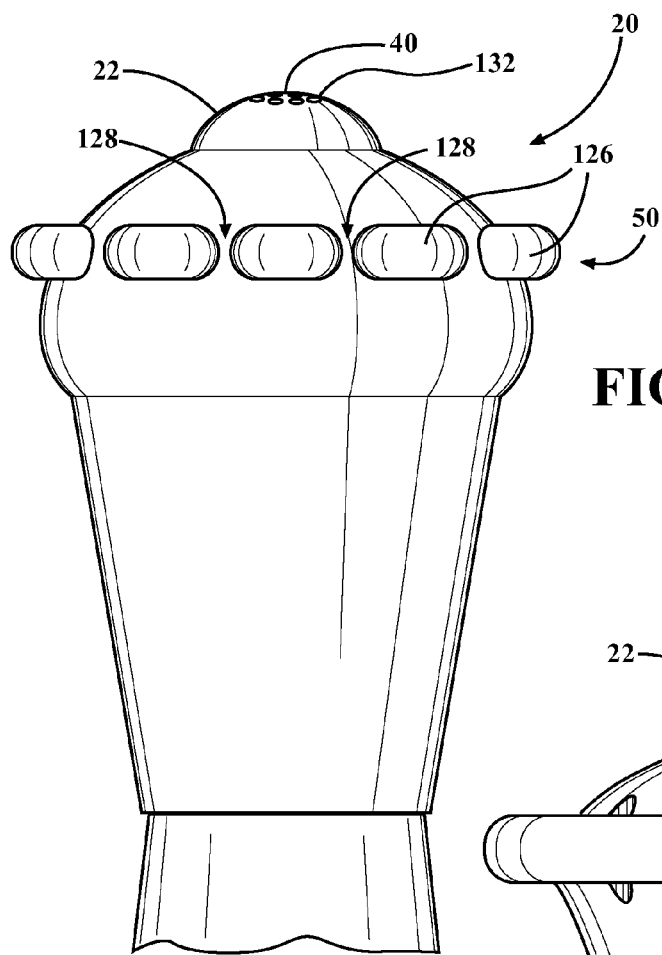
Figure 22:
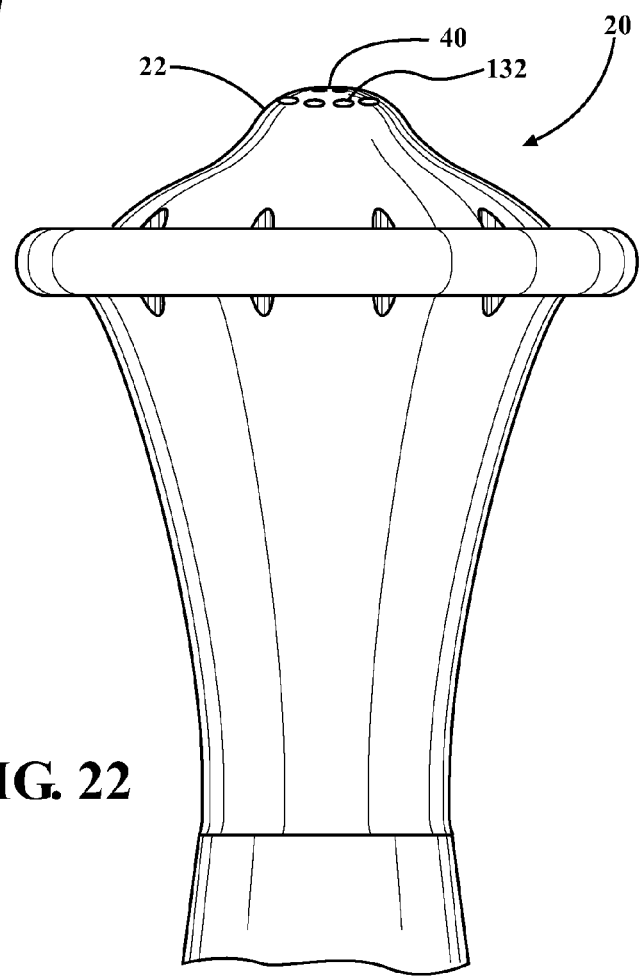
Figure 23:
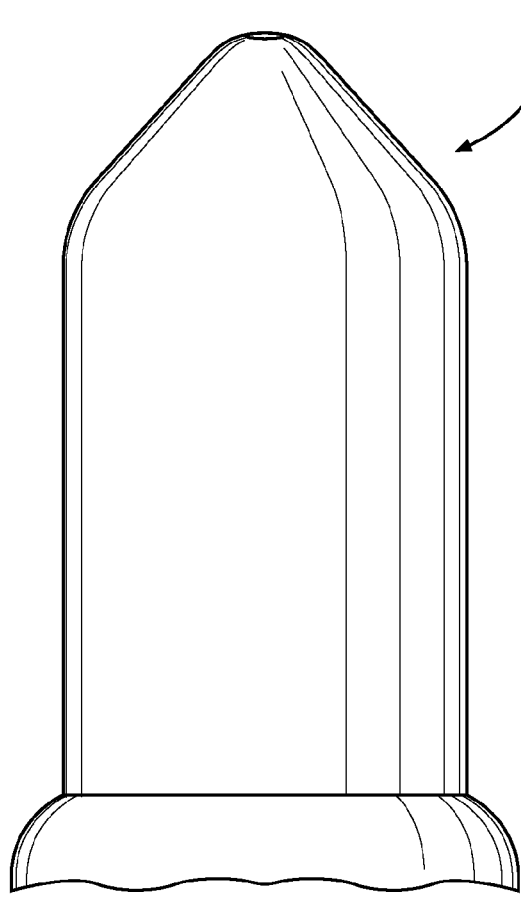
Figure 24:
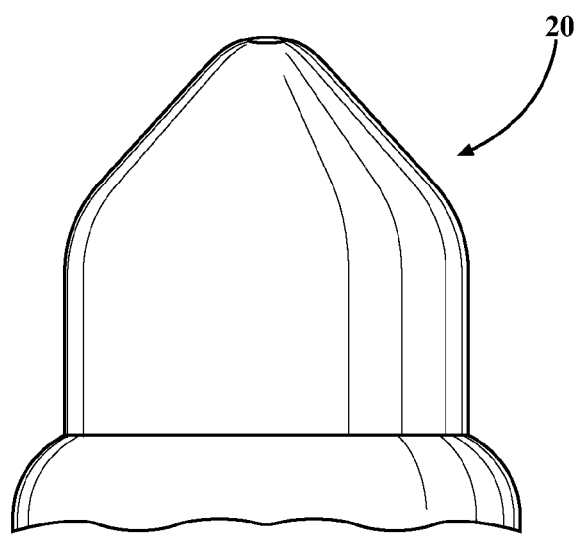
Figure 25:
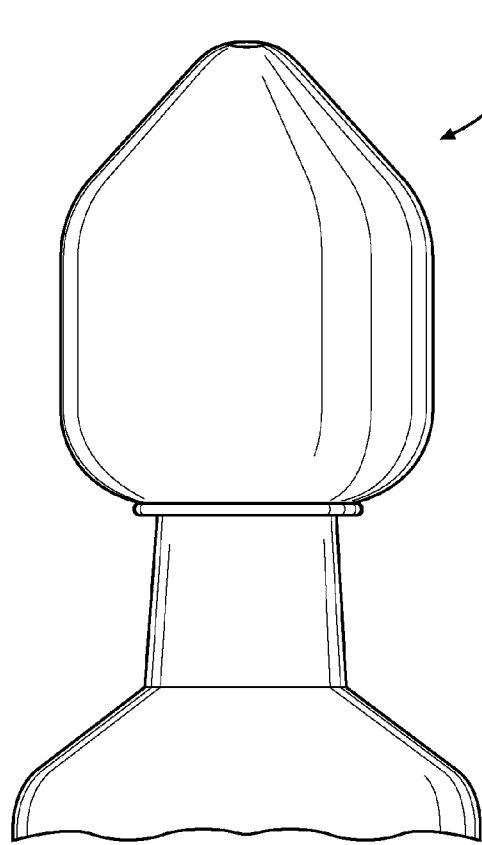
Figure 26:
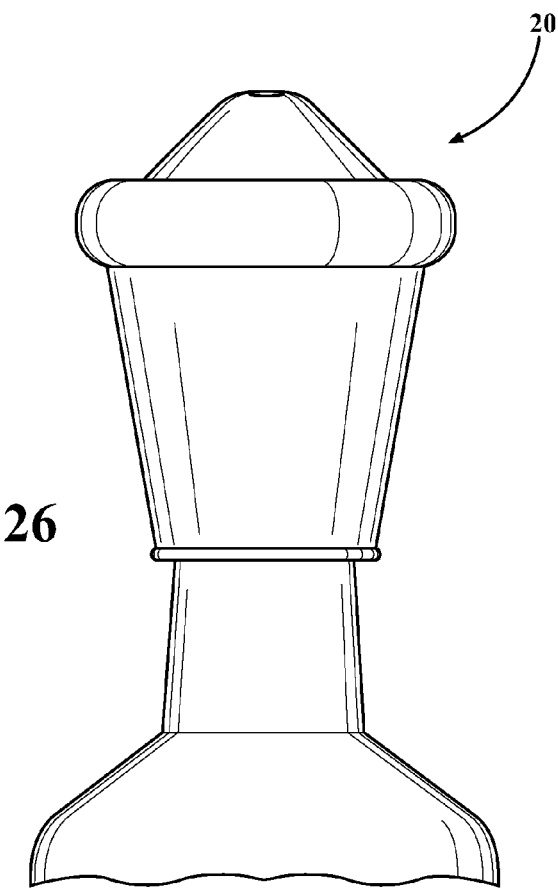
Figure 27:
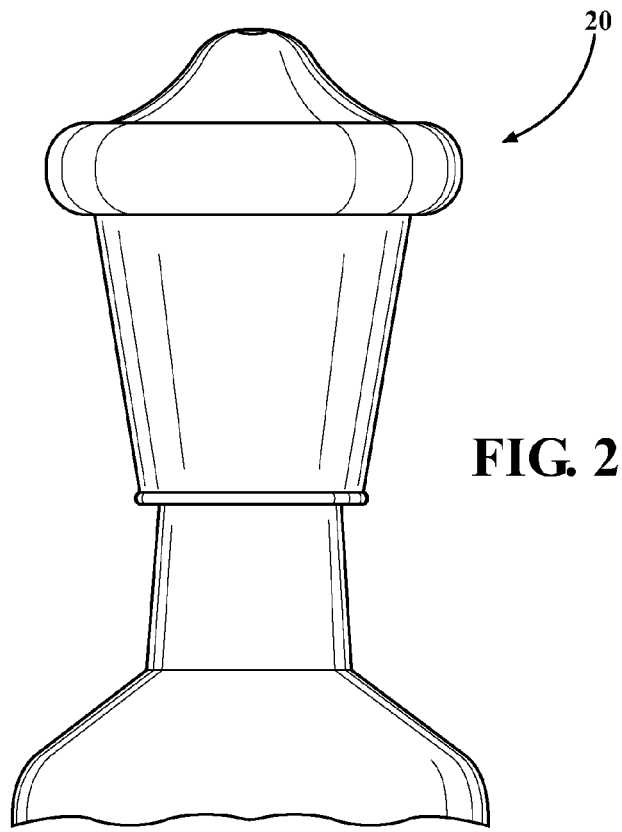
Figure 28:
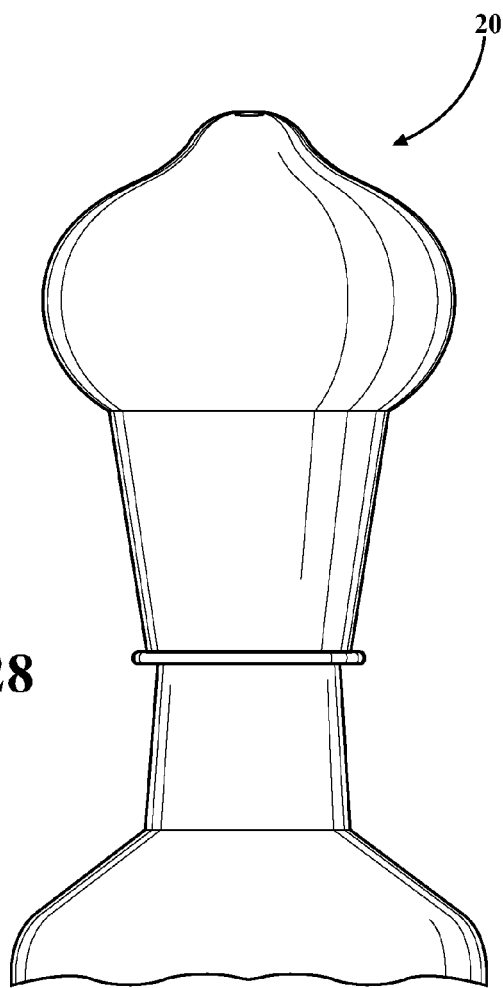
Figure 29:
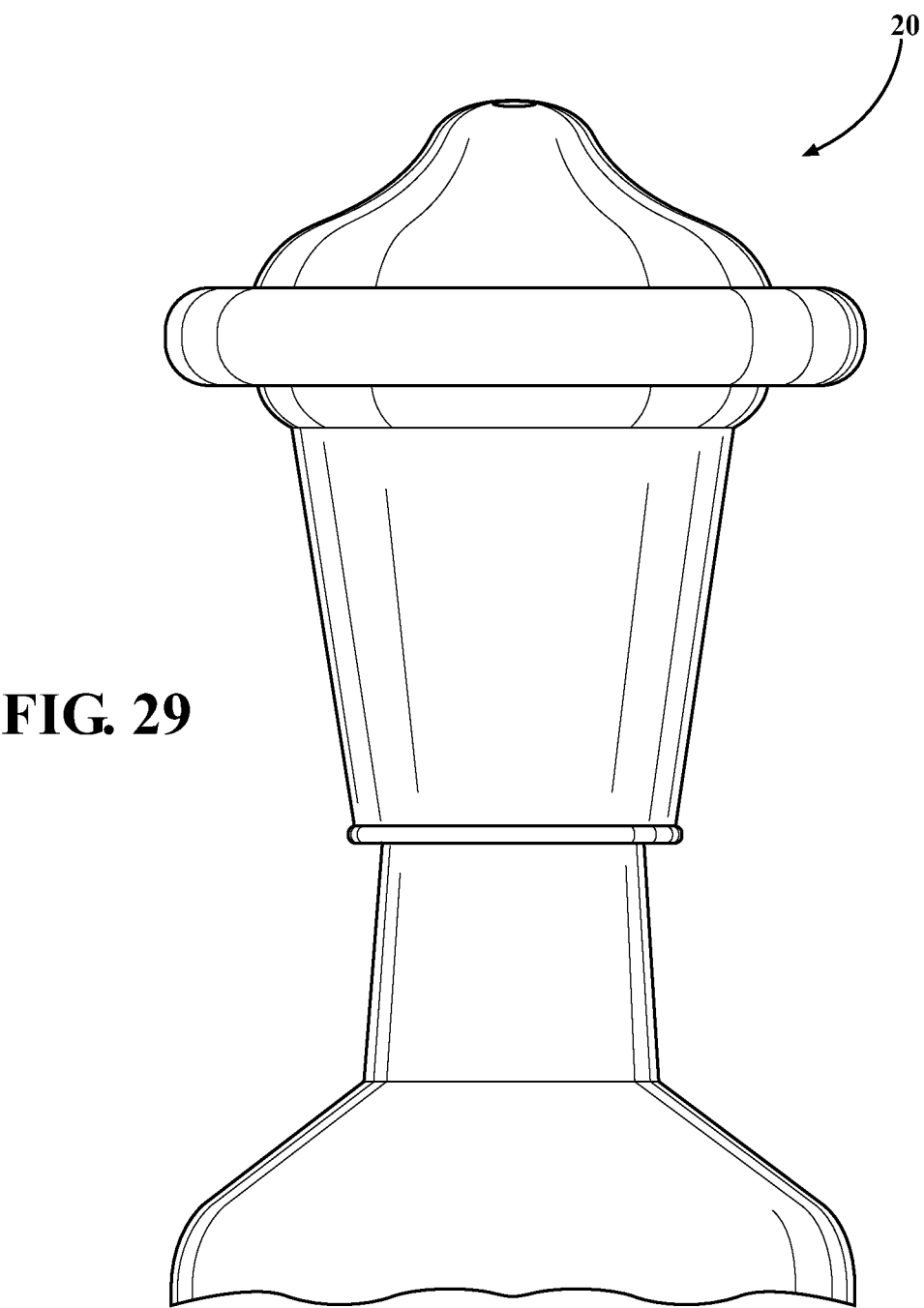

As illustrated in FIG. 21, the insertion-barrier ring 50 may include segments 126 made of protrusions. The smooth surface along the entire nozzle, including along the segments, allows a safer extraction in a case if the entire nozzle is accidentally inserted. The indentations 128 between the segments 126 may serve as the vacuum release paths. A plurality of openings 132 are disposed on the end face 22, in addition to the discharge opening 40 disposed in the center of the end face 22. The openings 130 may be disposed on an outer periphery of the end face 22, to provide a greater degree of comfort to the user.

Experimental Results

Experiments were conducted by the participants using various sizes and shapes for enema nozzles, with the following results:

Example 1

Dome-Shaped Nozzle

Diameter measurement: 5 cm
For some participants:
The 5 cm dome shape was too large to position between the buttocks and press against the anus to create a seal.
Because of the lack of an effective cap-to-anus seal, spillage occurred.

Example 2

Dome-Shaped Nozzle

Diameter measurement: 4 cm
For some participants:
The 4 cm dome cap is still too large to position between the buttocks to create a seal at the anus.
Spillage occurred.

Example 3

Dome-Shaped Nozzle

Diameter measurement: 2.5 cm
For some participants:
The 2.5 cm dome cap is more easily positioned between the buttocks and an effective cap-to-anus seal was achieved.
Minor spillage occurred.
Locating center-point of anal opening with blunt dome tip did not provide sufficient tactile feedback to facilitate exact positioning.
Participant with prolapsed hemorrhoids reported mild discomfort from the blunt dome shape when the cap was pressed into position creating uneven pressure against the prolapsed hemorrhoid tissue.

Example 4

Cone-Shaped Nozzle

Diameter measurement: 2.5 cm
Certain participants report that:
The 2.5 cm cone tip was easier to position between the buttocks.
The smaller tip of the cone (rounded edges for comfort) made it easier to locate the center point of the anal opening than the dome-shaped tip.
The participant with prolapsed hemorrhoids reported less discomfort by using the cone-shaped nozzle both from locating the anal center. The non-blunt cone-shaped tip required less pressure against the anus to create a comfortable and consistent seal; while the dome-shaped tip required more pressure to be applied to create a seal as the curve of the dome was unevenly pressed against the delicate tissue unevenly and caused some discomfort.
The insertion-barrier at the base of the cone provided greater comfort and assurance that over-insertion would be thwarted by the insertion-barrier.
All participants reported that no spillage occurred with the cone-shaped tip as the smaller diameter at the tip of the cone gently coaxed the anal opening to relax and conform to the cone tip permitting the fluid to be easily evacuated into the rectal cavity.

Participants prefer the cone-shaped tip as it can automatically adjust to various sized users, from infants to large adults.

One participant reported that they administered an enema to an elderly spouse using the cone-shaped tip with tremendous ease, safety and comfort for the recipient.

Some participants indicated that positioning the cone-shaped cap between the buttocks and locating the anus was made easier when the cap was pre-lubricated as mentioned in the provisional patent as an optional feature.

As demonstrated by the above examples, the 2.5 cm diameter dome-shaped tip can be used effectively with practice. The 2.5 cm diameter cone-shaped cap with a 3 to 5 mm tip and 2 to 3 mm insertion barrier hip can be used more effectively.

The shape of the cone cap and insertion barrier hip is such that the manufacturing method of producing the caps using a one-cavity die can be achieved for the cone-shaped tip. The one-cavity die manufacturing method also achieves the desired result of producing a perfectly smooth cone with no seams coming in contact with delicate tissue.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A nozzle (20) for administering a fluid (23) from a container (12) into a human cavity or animal cavity (66) through an orifice (58) of the cavity (66), said nozzle comprising:
    a base portion (32) for coupling said nozzle to the container;
    a top face (22) spaced from said base portion (32) with said top face defining a discharge opening;
    an interior passageway (30) extending between said base portion and said top face along a vertical axis (44) for delivering the fluid from the container through the discharge opening and into the human cavity or the animal cavity through the orifice;
    a rim (24) disposed between said base portion and said top face with said rim projecting radially outward relative to said vertical axis; and
    a side wall (26) extending between said top face and said rim with said side wall being continuous and uninterrupted between said top face and said rim to define a predetermined configuration prohibiting access into said interior passageway and for conforming to a tissue surrounding the orifice to seal the orifice during delivery of the fluid from the container into the human cavity or the animal cavity.

2. The nozzle according to claim 1, further comprising an insertion barrier (50) at the rim of the nozzle having an outside diameter greater than an outside diameter of the rim of the nozzle, thereby defining an annular shoulder for precluding inadvertent insertion of the nozzle through the orifice.

3. The nozzle according to claim 2, wherein the insertion barrier is a cylindrical structure extending downward from the rim of the nozzle.

4. The nozzle according to claim 2, wherein the insertion barrier comprises:
    a circumferential outer surface (52) that surrounds the interior passageway; and
    a hip (54) disposed between an edge (55) of the circumferential outer surface and an outer edge (56) of the rim of the nozzle.

5. The nozzle according to claim 2, wherein the insertion barrier comprises release openings (72) for allowing air to pass and prevent a vacuum when extracting an inadvertently inserted nozzle from the orifice.

6. The nozzle according to claim 2, wherein the insertion barrier is a ring.

7. The nozzle according to claim 1, wherein the discharge opening is made up of a plurality of openings in the top face of the nozzle.

8. The nozzle according to claim 1, wherein the side wall (26) is in the form of a dome structure (100) that surrounds the interior passageway (30) and converges towards the top face of the nozzle.

9. The nozzle according to claim 8, wherein the dome has a curvature of the same sign along an entire surface of the dome.

10. The nozzle according to claim 1, wherein the side wall has a curvature that changes sign at least once along a surface of the side wall.

11. The nozzle according to claim 1, wherein the interior passageway narrows towards the discharge opening of the nozzle so as to accelerate the flow of fluid through the passageway as the fluid approaches the discharge opening.

12. A device for administering a fluid (23) into a human cavity or animal cavity (66) through an orifice (58), said assembly comprising:
    a container (12) for housing the fluid; and
    a nozzle (20) coupled to said container for delivering the fluid from said container into the human cavity or the animal cavity, said nozzle having:
        a base portion (32) selectively mounted directly to said container,
        a top face (22) spaced from said base portion (32) with said top face defining a discharge opening,
        an interior passageway (30) extending between said base portion and said top face along a vertical axis (44) for delivering the fluid from said container through the discharge opening and into the human cavity or the animal cavity through the orifice,
        a rim (24) disposed between said base portion and said top face and projecting radially outward relative to said vertical axis, and
        a side wall (26) extending between said top face and said rim with said side wall being continuous and uninterrupted between said top face and said rim to define a predetermined configuration prohibiting access into said interior passageway and for conforming to a tissue surrounding the orifice to seal the orifice during delivery of the fluid from said container into the human cavity or the animal cavity.

13. The device according to claim 12, wherein the nozzle further includes:
    an elongated portion (31) that surrounds the interior passageway (30) and extends from a feeding portion of the container towards the rim of the nozzle; and
    a barrier ring disposed between the rim of the nozzle and the elongated portion.

14. A method of administering fluid from a container into a human cavity or an animal cavity through an orifice of the cavity utilizing a nozzle connected to the container, the nozzle having a top face, a radially projecting rim and a side wall extending between the top face and the rim with the side wall being continuous and uninterrupted between the top face and the rim to define a predetermined configuration prohibiting access into the interior passageway, said method comprising:

pressing the nozzle against the orifice without penetrating the orifice and with sufficient pressure to create a leak-tight seal between tissue surrounding the orifice and the side wall of the nozzle, and squeezing the container so as to force the fluid contained in the container to exit the top face in the nozzle and enter the cavity through the orifice.

15. A nozzle (20) for administering a fluid (23) from a container (12) into a human cavity or animal cavity (66) through an orifice (58) of the cavity (66), said nozzle comprising:

a base portion (32) for coupling mounting said nozzle to the container;

a top face (22) spaced from said base portion (32) with said top face defining a discharge opening;

an interior passageway (30) extending between said base portion and said top face along a vertical axis (44) for delivering the fluid from the container through the discharge opening and to said top face into the human cavity or the animal cavity through the orifice;

a rim (24) disposed between said base portion and said top face with said rim projecting radially outward relative to said vertical axis; and a side wall (26) extending between said top face and said rim and having a predetermined configuration for conforming to a tissue surrounding the orifice to seal the orifice during delivery of the fluid from the container into the human cavity or the animal cavity;

wherein said side wall forms a cone comprising a straight conical surface that extends from said top face to said rim for exerting even pressure on tissue surrounding the orifice when pressed against the tissue.

16. The nozzle according to claim 15, further comprising an insertion barrier (50) at the rim of the nozzle having an outside diameter greater than an outside diameter of the rim of the nozzle, thereby defining an annular shoulder for precluding inadvertent insertion of the nozzle through the orifice.

17. A nozzle (20) for administering a fluid (23) from a container (12) into a human cavity or animal cavity (66) through an orifice (58) of the cavity (66), said nozzle comprising:

a base portion (32) for coupling mounting said nozzle to the container;

a top face (22) spaced from said base portion (32) with said top face defining a discharge opening;

an interior passageway (30) extending between said base portion and said top face along a vertical axis (44) for delivering the fluid from the container through the discharge opening and to said top face into the human cavity or the animal cavity through the orifice;

a rim (24) disposed between said base portion and said top face with said rim projecting radially outward relative to said vertical axis; and a side wall (26) extending between said top face and said rim and having a predetermined configuration for conforming to a tissue surrounding the orifice to seal the orifice during delivery of the fluid from the container into the human cavity or the animal cavity, wherein said side wall comprises:

a nipple (102) at said top face of said nozzle; and a dome structure (100) that surrounds said interior passageway and extends downward from said nipple toward said base portion.

\* \* \* \* \*